(12) United States Patent
Limberg et al.

(10) Patent No.: US 12,357,551 B2
(45) Date of Patent: Jul. 15, 2025

(54) ANTIBACTERIAL CLEANSING COMPOSITION, USES AND METHODS

(71) Applicant: The Procter & Gamble Company, Cincinnati, OH (US)

(72) Inventors: Brian Joseph Limberg, Milford, OH (US); Sandra Liliana Tan, West Chester, OH (US); Wei Ji, Cincinnati, OH (US); Karl Shiqing Wei, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 320 days.

(21) Appl. No.: 18/319,962

(22) Filed: May 18, 2023

(65) Prior Publication Data

US 2023/0372219 A1    Nov. 23, 2023

Related U.S. Application Data

(60) Provisional application No. 63/344,678, filed on May 23, 2022.

(51) Int. Cl.
| | | |
|---|---|---|
| *A61K 8/00* | (2006.01) | |
| *A61K 8/34* | (2006.01) | |
| *A61K 8/41* | (2006.01) | |
| *A61K 8/46* | (2006.01) | |
| *A61K 8/49* | (2006.01) | |
| *A61Q 19/10* | (2006.01) | |

(52) U.S. Cl.
CPC .............. *A61K 8/463* (2013.01); *A61K 8/34* (2013.01); *A61K 8/41* (2013.01); *A61K 8/4913* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 6,106,851 A | 8/2000 | Beerse et al. | |
| 6,413,921 B1 | 7/2002 | Childers et al. | |
| 6,436,885 B2 | 8/2002 | Biedermann et al. | |
| 7,569,530 B1 | 8/2009 | Pan et al. | |
| 9,295,251 B1 | 3/2016 | Dyer et al. | |
| 9,409,853 B2 | 8/2016 | Schuch et al. | |
| 10,357,442 B2 | 7/2019 | Schelges et al. | |
| 10,441,522 B2 | 10/2019 | Schelges et al. | |
| 2002/0002124 A1* | 1/2002 | Biedermann | C11D 3/2082 510/382 |
| 2002/0098159 A1* | 7/2002 | Wei | A61Q 19/10 424/70.1 |
| 2003/0235550 A1 | 12/2003 | Pan et al. | |
| 2005/0271606 A1 | 12/2005 | Iwasaki et al. | |
| 2005/0271711 A1 | 12/2005 | Lynch et al. | |
| 2007/0232508 A1 | 10/2007 | Oshimura | |
| 2022/0023193 A1 | 1/2022 | Wu et al. | |
| 2023/0014524 A1 | 1/2023 | Wei et al. | |

FOREIGN PATENT DOCUMENTS

| | | |
|---|---|---|
| CN | 107693439 A | 2/2018 |
| CN | 110251611 A | 9/2019 |
| DE | 112007001469 T5 | 6/2009 |
| EP | 0259249 A2 | 3/1988 |
| WO | 0128552 A2 | 4/2001 |
| WO | 0152811 A1 | 7/2001 |
| WO | 0153443 A1 | 7/2001 |
| WO | 02078667 A1 | 10/2002 |
| WO | 2017112567 A1 | 6/2017 |
| WO | 2017132356 A1 | 8/2017 |
| WO | 2020212958 A1 | 10/2020 |

OTHER PUBLICATIONS

PCT Search Report and Written Opinion for PCT/US2023/023168 dated Oct. 18, 2023; 12 pages.
All Office Actions; U.S. Appl. No. 17/846,440, filed Jun. 22, 2022.

\* cited by examiner

*Primary Examiner* — Necholus Ogden, Jr.
(74) *Attorney, Agent, or Firm* — Alexandra S. Anoff

(57) ABSTRACT

An antibacterial cleansing composition including from about 0.01% to about 1% of chloroxylenol by weight of the composition; from about 5% to about 15% of sodium lauryl sulfate by weight of the composition; from about 1% to about 5% of a co-surfactant by weight of the composition, wherein the co-surfactant is selected from zwitterionic surfactant, amphoteric surfactant, nonionic surfactant, or combinations thereof; wherein the weight ratio of sodium lauryl sulfate to the co-surfactant ranges from about 3:1 to about 5:1; and wherein the composition comprises a pH of from about 2 to about 5.

15 Claims, No Drawings

ANTIBACTERIAL CLEANSING COMPOSITION, USES AND METHODS

FIELD OF THE INVENTION

The present application generally relates to an antibacterial cleansing composition, uses and methods relating thereto. The antibacterial cleansing composition comprises chloroxylenol; sodium lauryl sulfate and a co-surfactant; wherein the weight ratio of sodium lauryl sulfate to the co-surfactant ranges from about 3:1 to about 5:1; and wherein the composition comprises a pH of from about 2 to about 5.

BACKGROUND OF THE INVENTION

Human health is impacted by many microbial entities or microbials such as germs, bacteria, fungi, yeasts, molds, viruses and the like. For example, infection by microbial entities or microbials including various viruses and bacteria cause a wide variety of sicknesses and ailments. To reduce such infections, people frequently wash their skin with a cleansing composition. Cleansing compositions have traditionally been marketed in a variety of forms such as bar soaps, creams, lotions, and gels.

Washing with a cleansing composition, such as an antimicrobial soap can remove dirt and germs from skin. Removal of the viruses and bacteria is due to the surfactant behavior of the soap and the mechanical action of the wash procedure. Antibacterial soaps typically include soaps in combination with one or more actives, for example, antimicrobial agents; which can be in the form of a bar of soap. When the skin is washed with an antimicrobial soap, such as a bar soap, the surfactant of the soap typically removes most of the microbial entities or microbials on the skin, while the antimicrobial agent deposits at least in part onto the skin to provide residual protection against subsequent invasion.

Bacteria found on the skin can be divided into two groups: resident and transient bacteria. Resident bacteria are gram-positive bacteria which are established as permanent micro-colonies on the surface and outermost layers of the skin and play a relevant, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two sub-classes: Gram-positive and gram-negative bacteria. Gram-positive bacteria include pathogens such as *Staphylococcus aureus*. Gram-negative bacteria include pathogens such as *Escherichia coli*. Gram-negative bacteria are generally distinguished from gram-positive by an additional protective cell membrane which generally results in the gram-negative bacteria being less susceptible to topical antibacterial actives.

Given the health impacts of bacteria like *Staphylococcus aureus*, there is still a need to formulate an antibacterial cleansing composition which provides improved germ reduction on the skin.

Cleansing compositions have been traditionally marketed in a variety of forms such as bar soaps, creams, lotions, and gels. Typically, these products need to satisfy a number of criteria to be acceptable to consumers such as acceptable viscosity to deliver the actives of the composition. These criteria include cleansing effectiveness, skin feel, mildness to skin, hair, and ocular mucosae, and lather volume. Ideal cleansers should gently cleanse the skin or hair, cause little or no irritation, and should not leave the skin or hair overly dry after frequent use.

Hence, there is also a need to formulate an antibacterial cleansing composition which has sufficient rheological properties to be consumer acceptable and to deliver the actives of the composition.

SUMMARY OF THE INVENTION

An antibacterial cleansing composition is provided and comprises:
  a) from about 0.01% to about 1% of chloroxylenol by weight of the composition;
  b) from about 5% to about 15% of sodium lauryl sulfate by weight of the composition;
  c) from about 1% to about 5% of a co-surfactant by weight of the composition, wherein the co-surfactant is selected from zwitterionic surfactant, amphoteric surfactant, nonionic surfactant, or combinations thereof;
  d) wherein the weight ratio of sodium lauryl sulfate to the co-surfactant ranges from about 3:1 to about 5:1, preferably from about 7.5:2.5 to about 8:2; and wherein the composition comprises a pH of from about 2 to about 5.

A method of washing hands and washing away about 99% of bacteria is provided and comprises the following steps in that order:
  a) providing a container adapted to contain the antibacterial cleansing composition as set out herein;
  b) dispensing the antibacterial cleansing composition into palms of a user's hands;
  c) optionally lather by rubbing palms together;
  d) spread the antibacterial cleansing composition across the palms, back of hands, between fingers, and/or under nails;
  e) rinse hands;
  f) optionally dry;
  g) wherein the antibacterial cleansing composition washes away about 99% of bacteria.

A liquid hand wash composition is provided and comprises:
  a) from about 7% to about 9%, preferably from about 7.5% to about 8% of sodium lauryl sulfate by weight of the composition;
  b) from about 1.75% to about 3.0%, preferably from about 2.00% to about 2.5% of cocamidopropyl betaine by weight of the composition;
  c) wherein the weight ratio of sodium lauryl sulfate to cocamidopropyl betaine ranges from about 7.5:2.5 to about 8:2;
  d) from about 0.40% to about 0.60% of chloroxylenol by weight of the composition; and wherein the composition comprises a pH of from about 4 to about 5 and a viscosity of from about 3,000 cps to about 25,000 cps.

DETAILED DESCRIPTION OF THE INVENTION

Definitions of Terms

In this document, including in all embodiments of all aspects of the present invention, the following definitions apply unless specifically stated otherwise.

All percentages are by weight (w/w) of the composition, unless otherwise specified. "% wt." means percentage by weight. References to 'parts' e.g. a mixture of 1 part X and 3 parts Y, is a ratio by weight. All ratios or percentages are weight ratios or weight percentages unless specifically stated otherwise.

An "active composition" is the composition absent water, and an "active ingredient" is the ingredient absent its water.

"QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 25° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level and do not include carriers or by-products that may be included in commercially available materials.

Herein, "comprising" means that other steps and other ingredients can be in addition. "Comprising" encompasses the terms "consisting of" and "consisting essentially of". The compositions, methods, uses, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "free of" as used herein means that the composition comprises 0% of an ingredient by weight of the composition, thus no detectable amount of the stated ingredient.

The term "substantially free of" as used herein means less than about 1%, less than about 0.8%, less than about 0.5%, less than about 0.3%, or less than an immaterial amount of by weight of the composition.

Herein "Comp. Ex." or "C. Ex." means comparative example; and "Ex." means example.

The term "molecular weight" or "M. Wt." as used herein refers to the weight average molecular weight unless otherwise stated. The weight average molecular weight can be measured by gel permeation chromatography ("GPC").

The term "cleansing composition" as used herein refers to compositions intended for topical application to the skin for cleansing.

The term "perfume" as used herein refers to a mixture of volatile organic oils having a pleasant aroma wherein the perfume components have individual molecular weights between about 75 and 400 Daltons.

The term "mixtures" as used herein is meant to include a simple combination of materials and any compounds that may result from their combination.

The term "room temperature" refers to a temperature of 25° C.

The term "rinse-off" as used herein means the intended product usage includes application to skin and/or hair followed by rinsing and/or wiping the product from the skin and/or hair within a few seconds to minutes of the application step. The product is generally applied and rinsed in the same usage event, for example, a shower or washing one's hands.

The term "derivative" as used herein refers to structures which are not shown but which one skilled in the art would understand are variations of the basic compound.

The term "apply" or "application," as used in reference to a composition, means to apply or spread the compositions of the present invention onto the skin.

The term "dermatologically acceptable" means that the compositions or components described are suitable for use in contact with human skin tissue without undue toxicity, incompatibility, instability, allergic response, and the like.

The term "cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous p tissue are limited to those being cosmetically acceptable.

The methods as disclosed herein are cosmetic methods or non-therapeutic methods unless specifically stated otherwise.

The objects of the present invention are to provide antibacterial cleansing composition, methods and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Benefits

Human skin is the body's largest organ and is part of the body's natural defense to microbial attack. The natural skin defense is made up of a multitude of components. For example, the skin's natural defense includes the skin's ability to be a physical barrier, the pH of the skin, the skin microbiome, lipids on the skin, chemical components of the skin, etc.

Human skin's ability to provide a natural defense against microbial attack can be impacted by things with which it comes into contact during the day, like skin products.

Bacteria does not only stay on the skin surface, but also go deep into skin. It compromises skin barrier, causing skin sensitivity and irritation.

It was found that an antibacterial cleansing composition that comprises chloroxylenol, alternatively a mixture of chloroxylenol and pyrrolidone carboxylic acid can provide consistent antibacterial efficacy as shown in the standard Time-Kill study as set out herein. Immediate germ kill efficacy at both 30 seconds and 60 seconds contact time has been found with the antibacterial cleansing composition as disclosed herein Also, in order to deliver the antibacterial properties, the antibacterial cleansing composition needs to meet an optimized rheological profile. Surprisingly, the specific weight ratio of sodium lauryl sulfate to the co-surfactant could directly impact the viscosity of the antibacterial cleansing composition and help delivering the antibacterial active(s) onto the skin. When the weight ratio of sodium lauryl sulfate to the co-surfactant ranges from about 3:1 to about 5:1, preferably from about 7.5:2.5 to about 8:2, the rheology profile was sufficiently acceptable such that the antibacterial active(s) could be delivered onto skin. A relatively too thin composition could be prevented, which is also consumer preferred.

Antibacterial Cleansing Composition

Antibacterial Actives

The antibacterial cleansing composition comprises from about 0.01% to about 1%, preferably from about 0.10% to about 0.75%, more preferably from about 0.40% to about 0.60%, of chloroxylenol (also referred as 4-chloro-3,5-dimethylphenol or p-chloro-m-xylenol or PCMX) by weight of the composition.

Also, the antibacterial cleansing composition may comprise from about 0.005% to about 5%, preferably from about 0.02% to about 1%, more preferably from about 0.025% to about 0.15%, even more preferably from about 0.025% to about 0.05%, most preferably from about 0.025% to about 0.035%, of pyrrolidone carboxylic acid (also referred 2-pyrrolidone-5-carboxylic acid or pidolic acid) by weight of the composition.

Without wishing to be bound by theory, chloroxylenol alone, alternatively associated with pyrrolidone carboxylic acid, can provide consistent antibacterial efficacy especially against *Staphylococcus aureus* and/or any microorganisms as listed in Table 1 as set out below in the Test Method section.

Pyrrolidone carboxylic acid can also protonate the carboxylate functionalities on the phospholipid membrane of bacteria and reduce the tendency of the membrane to electronically repel anionic surfactants, thereby facilitating proper interaction between the present, anionic surfactants and the membrane.

Moreover, pyrrolidone carboxylic acid can help facilitating the creation of a low pH buffer on the surface of a substrate, thereby promoting human skin maintain its natural barrier against bacteria.

Surfactants

The antibacterial cleansing composition comprises: from about 5% to about 15% of sodium lauryl sulfate by weight of the composition; from about 1% to about 5% of a co-surfactant by weight of the composition, wherein the co-surfactant is selected from zwitterionic surfactant, amphoteric surfactant, nonionic surfactant, or combinations thereof; wherein the weight ratio of sodium lauryl sulfate to the co-surfactant ranges from about 3:1 to about 5:1, preferably from about 7.5:2.5 to about 8:2.

The antibacterial cleansing composition comprises from about 5% to about 15%, preferably from about 7% to about 9%, more preferably from about 7.5% to about 8% of sodium lauryl sulfate by weight of the composition.

In a specific aspect, the antibacterial cleansing composition may comprise from about 7% to about 9%, preferably from about 7.5% to about 8% of sodium lauryl sulfate by weight of the composition. In that specific aspect, the antibacterial cleansing composition is a liquid hand wash composition.

The antibacterial cleansing composition comprises from about 1% to about 5%, preferably from about 1.4% to about 3.0%, more preferably from about 2% to about 2.5% of a co-surfactant by weight of the composition. The co-surfactant is selected from the group consisting of zwitterionic surfactants, amphoteric surfactants, nonionic surfactants, and mixtures thereof.

Sodium lauryl sulfate and the co-surfactant as set out herein can provide a cleaning benefit, lather properties, and rheology properties to the compositions.

The antibacterial cleansing composition may include at least one of an amphoteric surfactant and a zwitterionic surfactant. Suitable amphoteric or zwitterionic surfactants may include those described in U.S. Pat. Nos. 5,104,646 and 5,106,609.

Amphoteric surfactants may include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

Alternatively or in addition, the co-surfactant included in the antibacterial cleansing composition described herein may comprise an amphoteric surfactant that is selected from the group consisting of sodium lauroamphoacetate, sodium cocoamphoacetate, disodium lauroamphoacetate, disodium cocodiamphoacetate, and mixtures thereof.

Zwitterionic surfactants suitable for use in the co-surfactants of the antibacterial cleansing composition described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, sulfate, phosphate, or phosphonate. The zwitterionic surfactant included in the antibacterial cleansing composition described herein may include one or more betaines, including cocamidopropyl betaine.

Alternatively, the amphoteric or zwitterionic surfactant may be selected from cocamidopropyl betaine, lauramidopropyl betaine, coco-betaine, lauryl betaine, cocoamphoacetate, cocoamphodiacetate, lauroamphoacetate, lauroamphodiacetate, lauramine oxide, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

The co-surfactants may comprise a zwitterionic surfactant, preferably a betaine and/or a sultaine, more preferably a zwitterionic surfactant selected from the group consisting of cocamidopropyl betaine, lauramidopropyl betaine, cocamidopropyl hydroxysultaine and mixtures thereof, even more preferably cocamidopropyl hydroxysultaine or cocamidopropyl betaine.

Preferably, the co-surfactant comprises cocamidopropyl betaine.

Nonionic surfactants suitable for use may include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants may include cocamide monoethanolamine, decyl glucoside, or a combination thereof.

Additional surfactants and other ingredients suitable for antibacterial cleansing compositions are found in US Pub. No. 2020/0046623, which is hereby incorporated by reference.

The antibacterial cleansing composition has a weight ratio of sodium lauryl sulfate to the co-surfactant ranging from about 3:1 to about 5:1, preferably from about 7.5:2.5 to about 8:2, more preferably of about 8:2.

Preferably, the co-surfactant may be cocamidopropyl betaine and the antibacterial cleansing composition has a weight ratio of sodium lauryl sulfate to cocamidopropyl betaine ranging from about 3:1 to about 5:1, preferably from about 7.5:2.5 to about 8:2, more preferably of about 8:2.

The antibacterial cleansing composition needs to reach an optimized rheological profile in order to deliver the antibacterial properties of the composition to the user's skin. Surprisingly, the specific weight ratio of sodium lauryl sulfate to the co-surfactant could directly impact the viscosity of the antibacterial cleansing composition. When the weight ratio of sodium lauryl sulfate to the co-surfactant ranges from about 3:1 to about 5:1, preferably from about 7.5:2.5 to about 8:2, the rheology profile was sufficiently consumer acceptable such that the antibacterial active(s) could be delivered onto skin.

The viscosity of the antibacterial cleansing composition may be from about 2.7 Pa·s (2,750 cps) to about 30 Pa·s (30,000 cps); preferably from about 3.0 Pa·s (3,000 cps) to about 25 Pa·s (25,000 cps); more preferably from about 3.4 Pa·s (3,400 cps) to about 24.25 Pa·s (24,250 cps).

pH

The pH of the antibacterial cleansing composition is from about 2.0 to about 5.0, preferably from about 3.0 to about 3.5, more preferably from about 3.1 to about 3.3.

The pH of the skin is typically naturally acidic, namely between about 4.5 and about 6.5. An acidic skin pH can help to activating specific enzyme to regulate skin activity and to balance the acid mantle of the skin. Such balanced acid mantle of the skin together with the antimicrobial peptides (AMPs) present in the skin layers skin maintain its natural barrier against bacteria.

The antibacterial cleansing composition may comprise an acidic pH as defined above to help the skin to reinforce its natural barrier against bacteria. Also, the acidic pH can help to promote the antibacterial properties of chloroxylenol; and if added, of pyrrolidone carboxylic acid.

A variety of compounds may be used to adjust the pH value of a composition. Such suitable compounds may include, but are not limited to, acetic acid, hydrochloric acid, sodium hydroxide, magnesium hydroxide, triethylamine, diethylamine, ethylamine, monoethanol amine, and any combinations thereof. The antibacterial cleansing composition may comprise greater than about 0% to about 2% of the pH adjusting agent, by the weight of the composition, preferably wherein the pH adjusting agent comprises citric acid.

Solubilizer

The antibacterial composition may include one or more solubilizers such as sugar alcohols or glycols. The sugar alcohols may include sorbitol. The glycols may include propylene glycol, dipropylene glycol, polyethylene glycol, derivatives thereof, and mixtures thereof. In one example, the antibacterial cleansing compositions can minimize the amount of solubilizers.

The antibacterial cleansing composition may include no more than about 10%, alternatively no more than about 5%, alternatively no more than about 3%, alternatively no more than about 1%, preferably greater than about 0% but less than about 3%, more preferably greater than about 0% but less than about 1%, by weight of the composition, of one or more solubilizers. The antibacterial cleansing composition may be substantially free of solubilizers, alternatively the composition may be free of solubilizers.

Structurant

The antibacterial cleansing composition may include one or more hydrophilic structurants such as carbohydrate structurants and gums. Some suitable carbohydrate structurants include raw starch (corn, rice, potato, wheat, and the like) and pregelatinized starch. Some suitable gums include carrageenan, guar gum and xanthan gum. The antibacterial cleansing composition may include from about 0.1% to about 30%, from about 2% to about 25%, or from about 4% to about 20%, by weight of the composition, of one or more carbohydrate structurants.

Humectant

The antibacterial cleansing composition may include one or more humectants. Examples of humectants may include polyhydric alcohols. Further, humectants such as glycerin can be included the antibacterial cleansing composition as a result of production or as an additional ingredient. For example, glycerin can be a by-product after saponification of the cleansing composition. Including additional humectant can result in a number of benefits such as improvement in hardness of the antibacterial cleansing composition, decreased water activity of the antibacterial cleansing composition, and reduction of a weight loss rate of the cleansing composition over time due to water evaporation. The antibacterial cleansing composition may comprise from greater than about 0% to about 10% of one or more humectants, by weight of the composition.

Inorganic Salt

The antibacterial cleansing composition may include one or more inorganic salts. Inorganic salts can help to maintain a particular water content or level of the composition and improve hardness of the composition. The inorganic salts can also help to bind the water in the composition to prevent water loss by evaporation or other means. The antibacterial cleansing composition may optionally include from 0.1% to about 15%, preferably from about 1% to about 12%, more preferably from about 2.5% to about 10.5%, by weight of the composition, of one or more inorganic salts. Examples of suitable inorganic salts may include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

Alternatively, the antibacterial cleansing composition may not include any inorganic salts.

Skin Benefit Agent

The antibacterial cleansing composition may include from about 0.5% to about 20% of one or more skin benefit agents, by weight of the composition.

Examples of suitable skin benefit agents may include petrolatum, glyceryl monooleate, mineral oil, natural oils, and mixtures thereof. Additional examples of skin benefit agents may include water insoluble or hydrophobic benefit agents.

Non-limiting examples of glycerides suitable for use as hydrophobic skin benefit agents herein may include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and mixtures thereof.

Non-limiting examples of alkyl esters suitable for use as hydrophobic skin benefit agents herein may include isopropyl esters of fatty acids and long chain esters of long chain (e.g., C10-C24) fatty acids, e.g., cetyl ricinoleate, non-limiting examples of which may include isopropyl palmitate, isopropyl myristate, cetyl riconoleate, and stearyl riconoleate. Other example may include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and mixtures thereof.

Non-limiting examples of polyglycerin fatty acid esters suitable for use as hydrophobic skin benefit agents herein may include decaglyceryl distearate, decaglyceryl diisostearate, decaglyceryl monomyriate, decaglyceryl monolaurate, hexaglyceryl monooleate, and mixtures thereof.

Preservative

The antibacterial cleansing composition may include one or more preservatives, generally included at less than about 2% by weight of the composition, preferably from 0.1% to 0.5% by weight of the composition. Such suitable preservatives may include, but are not limited to, benzyl alcohol, kathon, propylene glycol, hydroxy acetophenone, sodium benzoate, disodium ethylenediaminetetraacetic acid (EDTA), parabene, phenoxy ethanol, imidazolidinyl urea, and any mixture thereof.

The one or more preservatives may preferably comprise sodium benzoate, or a mixture of sodium benzoate and kathon. Kathon is composed of methylchloroisothiazolinone and methylisothiazolinone.

Alternatively, the one or more preservatives may preferably comprise salicylic acid, sodium benzoate, benzyl alcohol and kathon. Kathon is composed of methylchloroisothiazolinone and methylisothiazolinone. In that aspect or in any aspects, the one or more preservatives may comprise a mixture of salicylic acid and sodium benzoate, wherein a total amount of salicylic acid and sodium benzoate is from about 0.2% to about 0.9%, preferably from about 0.5% to about 0.85%, more preferably from about 0.75% to about 0.85%, by weight of the composition.

The weight ratio of salicylic acid to sodium benzoate may be from about 1:1.25 to about 1:1.10, preferably from about 1:1.175 to about 1:1.125.

Optional Ingredients

As can be appreciated, the compositions described herein may include a variety of optional components to tailor the properties and characteristics of the composition. As can be appreciated, suitable optional components are well known and can generally include any components which are physically and chemically compatible with the essential components of the compositions described herein. Optional components should not otherwise unduly impair product stability, aesthetics, or performance. Individual concentrations of optional components can generally range from about 0.001% to about 10%, by weight of the composition. Optional components can be further limited to components which will not impair the clarity of a translucent composition.

Optional components may include, but are not limited to, conditioning agents (including hydrocarbon oils, fatty esters, silicones), cationic polymers, anti-dandruff actives, and chelating agents. Additional suitable optional ingredients include but are not limited to colorants, particles, anti-microbials, foam boosters, anti-static agents, moisturizing agents, propellants, self-foaming agents, pH adjusting agents and buffers, preservatives, pearlescent agents, opacifiers, sensates, suspending agents, solvents, diluents, antioxidants, vitamins, and mixtures thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Fragrance Component

The antibacterial cleansing composition may comprise from about 0.1 wt. % to about 10 wt. % of a fragrance component by weight of the composition, preferably from about 0.2 wt. % to about 0.7 wt. % of a fragrance component by weight of the composition, more preferably from 0.2 wt. % to 0.6 wt. % of a fragrance component by weight of the composition.

Alternatively, the antibacterial cleansing composition may not include any fragrance component.

Typically the fragrance component may be a blend of perfumes and aroma chemicals. As used herein, "fragrance" is used to indicate any odoriferous material.

A wide variety of chemicals are known as fragrances, including alcohols, aldehydes, ketones, and esters. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of 500° C. or lower, 400° C. or lower, or 350° C. or lower. The BP of many fragrances are disclosed in *Perfume and Flavor Chemicals* (Aroma Chemicals), Steffen Arctander (1969). The ClogP value of the fragrances may be 0.1 or greater, 0.5 or greater, 1.0 or greater, and 1.2 or greater. As used herein, "ClogP" means the logarithm to the base 10 of the octanol/water partition coefficient. The ClogP may be readily calculated from a program called "CLOGP" which is available from Daylight Chemical Information Systems Inc., Irvine Calif., USA. Octanol/water partition coefficients are described in more detail in U.S. Pat. No. 5,578,563.

Suitable fragrances are also disclosed in U.S. Pat. Nos. 4,145,184, 4,209,417, 4,515,705, and 4,152,272. Non-limiting examples of fragrances include animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Other examples of suitable fragrances include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclogalbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltoiide, fenchone, fruity esters such as ethyl 2-methyl butyrate, galaxolide, geraniol and ester derivatives, helional, 2-heptonone, hexenol, α-hexylcinnamic aldehyde, hydroxycitronellal, indole, isoamyl acetate, isoeugenol acetate, ionones, isoeugenol, isoamyl isovalerate, iso E super, limonene, linalool, lilial, linalyl acetate, lyral, majantol, mayol, melonal, menthol, p-methylacetophenone, methyl anthranilate, methyl cedrylone, methyl dibydrojasmonate, methyl eugenol, methyl ionone, methyl-α-naphthyl ketone, methylphenylcarbinyl acetate, mugetanol, γ-nonalactone, octanal, phenyl ethyl acetate, phenylacetaldehyde dimethyl acetate, phenoxyethyl isobutyrate, phenyl ethyl alcohol, pinenes, sandalore, santaiol, stemone, thymol, terpenes, triplal, triethyl citrate, 3,3,5-trimethylcyclohexanol, γ-undecalactone, undecenal, vanillin, veloutone, verdox, and mixtures thereof.

In the antibacterial cleansing composition, the fragrance component may comprise ketone and/or aldehyde fragrance components. In addition, the fragrance component may further comprise any fragrances as set out just above.

Ketone fragrance components may be selected from alicyclic ketones such a β-ionone, terpene ketones such as 1-carvone, and macrocyclic ketones such as cyclopentadecanone.

Aldehyde fragrance components may be selected from fatty aldehydes such as 2,6-nonadienal, terpene aldehydes such as citral, and aromatic aldehydes such as α-hexylcinnamic aldehyde, cinnamaldehyde.

Thus, preferably the fragrance component may comprise ketone and/or aldehyde fragrance components, wherein the ketone and/or aldehyde fragrance components may be selected from the group consisting of acetophenone, adoxal, aldehyde C-12, aldehyde C-14, aldehyde C-18, α-amylcinnamic aldehyde, anisaldehyde, benzaldehyde, camphor, cinnamaldehyde, citral, cumin aldehyde, cyclamen aldehyde, damascones, fenchone, helional, 2-heptonone, α-hexylcinnamic aldehyde, hydroxycitronellal, ionones, lilial, lyral, melonal, p-methylacetophenone, methyl cedrylone, methyl ionone, methyl-α-naphthyl ketone, γ-nonalactone, octanal, phenylacetaldehyde dimethyl acetate, triplal, γ-undecalactone, undecenal, vanillin, veloutone, and mixtures thereof.

Rinse-Off Cleansing Compositions

The antibacterial cleansing composition may be a rinse-off cleansing composition. Rinse-off cleansing compositions may come in many forms. For example, a rinse-off cleansing composition may be in a liquid form and could be a body wash, shampoo, conditioning shampoo, moisturizing body wash, shower gel, skin cleanser, cleansing milk, in shower body moisturizer, pet shampoo, shaving preparation, etc. The rinse-off cleansing composition may be a hand wash or body wash composition, for example a liquid hand wash or a foaming hand wash composition.

The rinse-off cleansing composition may be water-based. It should be understood that an amount of water can be lost, i.e. evaporated, during a process of making a rinse-off cleansing composition, or subsequently, with water being absorbed by surrounding packaging (e.g. a cardboard carton), and the like. Thus, a rinse-off cleansing composition can also include materials that tend to bind the water such that the water can be maintained in the cleansing composition at the desired levels. Examples of such materials may include carbohydrate structurants and humectants such as glycerin. The rinse-off cleansing composition nay include water in the amount of more than about 80%, alternatively more than about 85%, alternatively more than about 88%, by total weight of the composition. However, it will be appreciated that a rinse-off cleansing composition can be anhydrous.

Liquid Hand Wash

A liquid hand wash composition is provided and comprises:
a) from about 7% to about 9%, preferably from about 7.5% to about 8% of sodium lauryl sulfate by weight of the composition;
b) from about 1.75% to about 3%, from about 2% to about 2.5% of cocamidopropyl betaine by weight of the composition, wherein the weight ratio of sodium lauryl sulfate to cocamidopropyl betaine ranges from about 7.5:2.5 to about 8:2;
c) from about 0.40% to about 0.60% of chloroxylenol by weight of the composition; wherein the composition comprises a pH of from about 4 to about 5 and a viscosity of from about 3 Pa·s (3,000 cps) to about 25 Pa·s (25,000 cps).

The liquid hand wash may comprise from about 0.025% to about 0.035% of pyrrolidone carboxylic acid by weight of the composition.

Preferably, the liquid hand wash composition may comprise about 8% sodium lauryl sulfate, about 2% cocamidopropyl betaine, and 0.05% of chloroxylenol.

More preferably, the liquid hand wash composition may comprise about 8% sodium lauryl sulfate, about 2% cocamidopropyl betaine, about 0.03% pyrrolidone carboxylic acid and 0.05% of chloroxylenol.

Methods

The antibacterial cleansing composition described herein can be intended for use as a hand wash.

A method of washing hands and washing away about 99% of bacteria is provided and comprises the following steps in that order:
a) providing a container adapted to contain the antibacterial cleansing composition as set out herein;
b) dispensing the antibacterial cleansing composition into palms of a user's hands;
c) optionally lather by rubbing palms together;
d) spread the antibacterial cleansing composition across the palms, back of hands, between fingers, and/or under nails;
e) rinse hands;
f) optionally dry; and
wherein the antibacterial cleansing composition washes away about 99% of bacteria.

The container may be a pump dispenser or a pump foam dispenser.

A user can wash their hands with hand wash as follows:
1) If using liquid hand wash, wet hands with clean, running water (warm or cold), optionally turn off the tap, and apply soap. If using foaming hand wash, rinsing hands before applying the soap is optional.
2) If using liquid hand wash, lather by rubbing palms together with the soap. Lather the backs of hands, between fingers, and under nails. If using foaming hand wash, spread the foam across the palms, back of hands, between fingers, and under nails.
3) It is recommended to scrub hands for at least 20 seconds.
4) Rinse hands well under clean, running water.
5) Dry hands using a clean towel or air dry them.

Washing hands with the antibacterial cleansing composition described herein can help skin maintain its natural barrier against bacteria.

Also, the antibacterial cleansing composition described herein can wash away about 99% of bacteria.

The antibacterial cleansing composition described herein can be an hydrating hand wash. It can have a fresh clean scent, nourishing aloe scent, ocean breeze scent, notes of citrus, notes of lavender, and/or notes of coconut.

The antibacterial cleansing composition described herein can help skin maintain its natural barrier against bacteria.

The antibacterial cleansing composition described herein can help maintain skin's protective barrier.

The antibacterial cleansing compositions described herein can enable the skin to be the first line of defense against bacteria.

The antibacterial cleansing composition can be readily dispersed by a pump and are freely pourable from any suitable container. In some examples, the antibacterial cleansing composition can be dispensed as a liquid or a foam from a suitable container by squeezing the container.

Alternatively, the antibacterial cleansing composition may be dispensed when a user actuates (e.g. pushes down on) the pump.

Alternatively, the antibacterial cleansing composition may be suitable for dispensing by a pump foamer, which is a non-aerosol way of dispensing the antibacterial cleansing composition as a foam that generally mixes air in a foaming chamber before discharging the composition.

Uses

All the limitations and aspects as disclosed hereinabove for the antibacterial cleansing composition might apply herein below.

An antibacterial cleansing composition as set out herein is provided for use as an antibacterial medicament in the form of a product to be applied to the human skin.

The antibacterial cleansing composition may be applied to an area of need of treatment.

The area of need of treatment may be a keratinous tissue surface. A keratinous tissue refers to keratin-containing layers positioned as the outermost protective covering of mammals which includes, but is not limited to, skin, hair, nails, or cuticles.

The area of need of treatment may be preferably the human skin surface, or scalp surface.

Preferably, the antibacterial cleansing composition as set out herein may be provided for use in a method of inhibiting or killing the growth of bacteria onto human skin.

More preferably, the antibacterial cleansing composition as set out herein may be provided for use in a method of inhibiting or killing the growth of bacteria onto human skin, wherein the bacteria is *Staphylococcus aureus*.

Alternatively, the antibacterial cleansing composition as set out herein may be provided for use in a method of inhibiting or killing the growth of bacteria onto human skin, wherein the bacteria is one as listed in Table 1 as detailed more below.

Indeed, as shown in the Example section, at least a 5-log or 99.999% reduction was observed for the 30 second and 60 second contact time intervals for all challenge microorganisms tested when assessing an antibacterial cleansing composition under the Time-Kill Test Method as disclosed herein. The start and end counts for test culture viability were within ±0.5 $Log_{10}$.

Non-therapeutic use of the antibacterial cleansing composition as set out herein for providing a cleansing benefit.

Non-therapeutic use of the antibacterial cleansing composition as set out herein for improving hand hygiene.

Test Methods

It is understood that the Test Methods that are disclosed in the Test Methods Section of the present application should be used to determine the respective values of the parameters of Applicants' invention as such invention is described and claimed herein.

Cone/Plate Viscosity Measurement Test Method

The viscosities of the examples are measured by a Cone/Plate Controlled Stress Brookfield Rheometer R/S Plus, by Brookfield Engineering Laboratories, Stoughton, MA. The cone used (Spindle C-75-1) has a diameter of 75 mm and 1° angle. The viscosity is determined using a steady state flow experiment at constant shear rate of 2 $s^{-1}$ and at temperature of 26.5° C. The sample size is 2.5 ml and the total measurement reading time is 3 minutes.

Assessment of Antimicrobial Activity Using a Time-Kill Test Method

Scope

The Time-Kill test method measures the in vitro reduction of a microbial population of test organisms after specified contact times to one product formulation. Hence, the test method measures the changes of a population of aerobic and/or anaerobic microorganisms within a specific sampling time when tested against antimicrobial test materials in vitro. The organisms used are standardized as to growth requirements and inoculum preparation and must grow under the conditions of the test. The primary purpose of this test method is to provide a set of standardized conditions and test organisms to facilitate comparative assessments of antimicrobial materials miscible in aqueous systems.

The Time-Kill evaluation of a product formulation (See Ex. 9 below) was performed using a modification of the ASTM Committee E35.15 standard test method E2783-11 (2016) "Standard Test Method for Assessment of Antimicrobial Activity for Water Miscible Compounds Using a Time-Kill Procedure" and Food and Drug Administration Safety and Effectiveness of Consumer Antiseptics; Topical Antimicrobial Drug Products for Over-the-Counter Human Use; Proposed Amendment of the Tentative Final Monograph; Reopening of Administrative Record. June 2016.

The antimicrobial properties of the test product were limited to the challenge microorganisms listed in Table 1 below following exposure within the specified sampling times of 30 and 60 seconds after inoculation.

TABLE 1

Study Parameters

| Contact Times | Organisms | Test Replicates | Population Controls |
|---|---|---|---|
| 30 & 60 seconds with the Test product | *Campylobacter jejuni* ATCC 33291 | 3 | 1 |
| | *Campylobacter jejuni* ATCC 49943 | 3 | 1 |
| | *Enterococcus faecalis* ATCC 19433 | 3 | 1 |
| | *Enterococcus faecalis* ATCC 29212 | 3 | 1 |
| | *Escherichia coli* ATCC 11775 | 3 | 1 |
| | *Escherichia coli* ATCC 25922 | 3 | 1 |
| | *Listeria monocytogenes* ATCC 7644 | 3 | 1 |
| | *Listeria monocytogenes* ATCC 19115 | 3 | 1 |
| | *Pseudomonas aeruginosa* ATCC 15442 | 3 | 1 |
| | *Pseudomonas aeruginosa* ATCC 27853 | 3 | 1 |
| | *Salmonella enterica serovar Enteritidis* ATCC 13076 | 3 | 1 |
| | *Salmonella enterica serovar Typhimurium* ATCC 14028 | 3 | 1 |
| | *Shigella sonnei* ATCC 9290 | 3 | 1 |
| | *Shigella sonnei* ATCC 25931 | 3 | 1 |
| | *Staphylococcus aureus* ATCC 6538 | 3 | 1 |
| | *Staphylococcus aureus* ATCC 29213 | 3 | 1 |
| | Methicillin-resistant *Staphylococcus aureus* (MRSA) ATCC 33591 | 3 | 1 |
| | Methicillin-resistant *Staphylococcus aureus* (MRSA) ATCC 33592 | 3 | 1 |
| | *Streptococcus pyogenes* ATCC 14289 | 3 | 1 |
| | *Streptococcus pyogenes* ATCC 19615 | 3 | 1 |

Apparatus

Incubators, capable of maintaining 35±1° C. and 42±1° C.

Incubator thermometers, NIST traceable

Vortex mixer

Calibrated, traceable minute/second timer

Refrigerator 2-8° C.

Refrigerator thermometer, NIST traceable

Adjustable pipettor, 10-100 µL, 20-200 µL, and 100-1000 µL capacity

Quebec colony counter

Traceable thermometer/clock/humidity monitor

Hand tally

Electronic balance, sensitive to 0.1 g

Anaerobe jars

Autoclave

Ultralow freezer, capable of maintaining −70° C.
Centrifuge
DensiCHEK Plus Instrument
Pipettors Materials Micropipette tips, 10-100 µL, 20-200 µL, and 100-1000 µL
Serological pipettes, 1, 2, 5, 10, and 25 mL
Test tubes
Disposable Petri dishes, 100×15 mm
Flasks or Containers
   Appropriate sizes with closures for preparation of culture medium and sterile deionized water.
   Volumetric, 100 and 1000 mL
BD GasPak EZ Campy Container System (BD PN 260680) for microaerophilic atmospheric conditions Reagents Neutralizer: dilution to sub-inhibitory levels in Letheen Blanks (LB) (MP088*)
Microbial Content Test (MCT) agar (MP107)
Trypticase Soy Agar (TSA) (MP064)
Phosphate Buffered Saline (PBS) (MP416)
Tryptic Soy Agar with 5% Sheep Blood (SBA) Commercially available from BD, PN 221261
Campy Cefex Agar (CCA) (MP329)
*Campylobacter* CFP Supplement—Commercially available from Acumedia, PN 7981—used as a supplement in CCA
Sterile Laked Horse Blood—Commercially available from Hemostat, PN LHB 250—used as a supplement in CCA
Sterile Deionized Water (DI water) (MP046)
As appropriate, media/chemicals/reagents were purchased sterile or sterilized via autoclaving.
The MP number refers to Q Laboratories media preparation number.

Method Description

Test Microorganism Preparation:
   Seed-lot culture maintenance techniques were used so that the viable microorganisms used for inoculation were not more than five passages removed from the original master seed lot.
For Bacteria:
   Propagated on SBA for 18-24 hours at 35±1° C. from a Q Laboratories frozen stock culture stored at −70° C.
   Transferred cultures onto TSA slants.
   Incubated each daily transfer at 35±1° C. for 24±2 hours.
   Performed daily transfers of each culture by aseptically transferring growth to fresh agar.
For *Campylobacter jejuni*:
   Propagated on CCA for 48±2 hours at 42±1° C. in microaerophilic atmospheric conditions from a Q Laboratories frozen stock culture stored at −70° C.
   Transferred cultures onto CCA.
   Incubated each transfer at 42±1° C. for 48±2 hours.
   Performed transfers of each culture by aseptically transferring growth to fresh agar.
   Washed each agar slant with 3 mL of PBS to harvest cells. A minimum starting inoculum level of $1.0 \times 10^9$ CFU/mL was used for testing. To verify the inoculum concentration, the cell density was measured using the DensiCHEK Plus Instrument to ensure it was within the range 3.5-4.0 McFarland.
   After harvesting the cells, any culture suspensions <3.5 McFarland were centrifuged at 4,500 rpm for 15 minutes. The supernatant was discarded and the pellet re-suspended with 3 mL of PBS, and the concentration verified.
Test Procedure:
   Used a 0.1 mL aliquot of the $10^9$ CFU/mL standardized suspension of challenge organism to inoculate a 10.0 mL portion of the product formulation.
   Vortexed the suspension.
   Held for the contact times of 30±2 and 60±3 seconds.
   At each contact time, 1.0 mL of inoculated product was used to make ten-fold serial dilutions in LB neutralizer.
   Plated the dilutions via pour plate technique in duplicate.
   Plated the *Campylobacter jejuni* in duplicate using CCA and incubated in microaerophilic atmospheric conditions at 42±1° C. for 48±2 h.
   Plated all other organisms in duplicate using MCT and incubated in aerobic atmospheric conditions at 35±1° C. for 48±2 h.
   Counted colonies and recorded as CFU/plate to determine surviving organisms.
   Each sample, contact time, and organism was plated an additional two times, for a total of three replicates.

Study Controls

Test Culture Viability:
   To verify the viability of the inoculum, it was enumerated at the start and end of the testing phase. Inoculum populations were determined by preparing ten-fold serial dilutions of each challenge organism suspension in duplicate by standard microbiological procedures.
   Colonies were enumerated and recorded as CFU/plate. Duplicate plates were averaged and multiplied by the dilution factor to calculate the microbial population (CFU/mL) of the suspension.
   The start and end counts of the testing phase must be within ±0.5 $Log_{10}$ for test to be valid.
Population Control:
   Determined inoculum populations by inoculating and analyzing an aliquot of sterile water at the same volume and under the same conditions as the test products.
   Plated the inoculum suspension after the longest contact time interval specified in the protocol.
   Incubated inoculum plates at the specified temperature and time as appropriate for the test organism.
Neutralization Evaluation:
   The test methods outlined in this section ensure that no components of the neutralizing procedure exert a detectable amount of inhibitory effect on the microorganisms targeted for recovery.
   The test methods outlined in this section also ensure the ability of the neutralization procedure to inactivate the antimicrobial properties of the test products.
   Neutralization procedures were conducted according to ASTM Method E1054-08 (Reapproved 2013) *Standard Test Methods for Evaluation of Inactivators of Antimicrobial Agents*.
Neutralizer Effectiveness Test (NET):
   Mixed 1.0 mL of product with 9.0 mL of neutralizer followed by the addition of 0.1 mL of the test culture that had been serially diluted in PBS to produce a final concentration of 30-100 CFU/mL.

Mixed the suspension of cells, product, and neutralizer thoroughly, plated immediately, held for the longest contact time of the time-kill analysis and plated a second time.

Repeated the procedure just above an additional two times, for a total of three replicates. Conducted the NET evaluation for each organism type represented in the study (Gram positive, Gram negative, microaerophilic) using appropriate media, incubation time, and temperature for the chosen organism.

To demonstrate effective neutralization of the test product, the average difference between the NET initial and final plate counts cannot exceed 0.2 $Log_{10}$.

Neutralizer Toxicity Test (NTT):

Mixed 1.0 mL of PBS with 9.0 mL of neutralizer followed by the addition of 0.1 mL of the test culture that had been serially diluted in PBS to produce a final concentration of 30-100 CFU/mL.

Mixed the suspension of the cells, PBS, and neutralizer thoroughly, plated immediately, held for the longest contact time of the time-kill analysis and plated a second time.

Repeated the procedure just above an additional two times, for a total of three replicates. Conducted the NTT evaluation for each organism type represented in the study (Gram positive, Gram negative, microaerophilic) using appropriate media, incubation time, and temperature for the chosen organism.

To demonstrate that no components of the neutralizing procedure exerted an inhibitory effect, the difference between the NTT initial and final plate counts could not exceed 0.2 $Log_{10}$.

Test Organism Viability (TOV):

Mixed 10.0 mL of PBS, followed by the addition of 0.1 mL of the test culture that had been serially diluted in PBS to produce a final concentration of 30-100 CFU/mL.

Mixed the suspension the cells and PBS, plated immediately, held for the longest contact time of the time-kill analysis and plated a second time.

Repeated the procedure just above an additional two times, for a total of three replicates. Conducted the TOV evaluation for each organism type represented in the study (Gram positive, Gram negative, microaerophilic) using appropriate media, incubation time, and temperature for the chosen organism.

Media Quality Controls:

For MCT:

Inoculated duplicate plates with 1-100 CFU of *Bacillus subtilis* ATCC 6633, *Staphylococcus aureus* ATCC 6538, *Pseudomonas aeruginosa* ATCC 9027, *Escherichia coli* ATCC 8739, *Aspergillus brasiliensis* ATCC 16404 and *Candida albicans* ATCC 10231 and incubated at 30-35° C. for 3 days or less.

Inoculated duplicate plates of an equivalent medium with 1-100 CFU of *Bacillus subtilis* ATCC 6633, *Staphylococcus aureus* ATCC 6538 and *Pseudomonas aeruginosa* ATCC 9027, *Escherichia coli* ATCC 8739, *Aspergillus brasiliensis* ATCC 16404 and *Candida albicans* ATCC 10231 and incubated at 30-35° C. for 3 days or less.

Incubated 1 plate at 30-35° C. for 3 days or more to serve as the sterility control.

Comparable growth acceptance was within 5-200% between the media. Sterility acceptance was no growth.

For CCA:

Inoculated duplicate plates with 1-100 CFU of *Campylobacter jejuni* ATCC 49943 and incubated in microaerophilic atmospheric conditions at 42±1° C. for 48±2 h.

Inoculated duplicate plates of an equivalent medium with 1-100 CFU of *Campylobacter jejuni* ATCC 49943 and incubated in microaerophilic atmospheric conditions at 42±1° C. for 48±2 h.

Incubated 1 plate in microaerophilic atmospheric conditions at 42±1° C. for 48±2 h.

Comparable growth acceptance was within 50-200% between the media. Sterility acceptance was no growth.

Sterility Assessment for PBS, LB, TSA Slant, and DI Water:

Incubated 1 tube of each medium at 30-35° C. for 1 day or more to serve as the sterility controls.

After incubation, streaked to a general growth agar. Incubated for 1 day or less at 30-35° C.

The acceptance criteria was no growth from the sterility controls.

Calculations

Neutralization Evaluations:

If no difference (<0.2 Log) existed between the average initial and final counts, the number of surviving microorganisms from the final analysis of the Neutralizer Effectiveness and Neutralizer Toxicity were statistically compared to the final counts obtained in Test Organism Viability analysis using a Student's t test (p>0.05).

Neutralization was considered adequate if the recovery of organisms from the Neutralizer Effectiveness and Neutralizer Toxicity tests were not significantly different from the recovery of organisms from the Test Organism Viability (p>0.05).

A t-test assuming equal variance was used to determine the actual p value of the neutralization evaluations.

$$t = \frac{x_1 - x_2}{\sqrt{s^2\left(\frac{1}{n_1} + \frac{1}{n_2}\right)}}$$

$x_1$ and $x_2$=the sample means
$s^2$=Pooled sample variance
$n_1$ and $n_2$=sample sizes
t=Student t quantile with $n_1+n_1-$ degrees of freedom A logarithmic transformation measuring surviving microbial populations of the population control and test replicates for each microorganism was performed.

The Log reduction was calculated as follows:
TP=Test Product
PC=Population Control
LR=Log Reduction
LR=Log$_{10}$PC−Log$_{10}$TP
Percent reduction was calculated as follows:
PR=Percent Reduction $$PR = \left\{\frac{PC\ CFU - TP\ CFU}{PC\ CFU}\right\} \times 100$$

Note: Calculate <1.0×10$^1$ as "10" to obtain the percent and Log reduction.

The difference between initial and final time points of the test organism viability was calculated as follows:
IC=Initial Count
FC=Final Count
TOV=Test Organism Viability Difference
TOV=Log$_{10}$IC−Log$_{10}$FC
Note: No statistically significant difference was observed during testing between initial and final time points (<0.5 Log$_{10}$.)

Performance Criteria

In order to demonstrate acceptable kill, a percent reduction from the initial microbial population, calculated from the Log$_{10}$ baseline counts of the surviving population must have been observed within the time intervals for each challenge organism tested.

Acceptance Criteria

The study controls below must have performed according to the criteria detailed for the data to be considered acceptable.

The start and end counts for test culture viability must be within ±0.5 Log$_{10}$ for test to be valid.

Neutralization was considered adequate if the recovery of organisms from the Neutralizer Effectiveness Test was not significantly different from the recovery of organisms from the Test Organism Viability (p>0.05).

The media must meet the specifications listed in Media Quality Controls as set out above.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following examples were prepared with no fragrance:
Compositions (wt. %)

|  | C. Ex. A | C. Ex. B | Ex. 1 | Ex. 2 | C. Ex. C | C. Ex. D |
|---|---|---|---|---|---|---|
| Sodium Lauryl Sulfate (SLS)[1] | 9.00 | 8.50 | 8.00 | 7.50 | 7.00 | 6.00 |
| Cocamidopropyl Betaine (CAPB)[2] | 1.00 | 1.50 | 2.00 | 2.50 | 3.00 | 4.00 |
| Sodium benzoate | 0.25 | 0.25 | 0.25 | 0.25 | 0.25 | 0.25 |
| Disodium EDTA | 0.10 | 0.10 | 0.10 | 0.10 | 0.10 | 0.10 |
| Chloroxylenol[3] | 0.50 | 0.50 | 0.50 | 0.50 | 0.50 | 0.50 |
| Citric Acid | 1.30 | 1.30 | 1.30 | 1.30 | 1.30 | 1.30 |
| Benzyl Alcohol | 0.30 | 0.30 | 0.30 | 0.30 | 0.30 | 0.30 |
| Methylchloroisothiazolinone, Methylisothiazolinone[4] | 0.03 | 0.03 | 0.03 | 0.03 | 0.03 | 0.03 |
| Fragrance | 0.00 | 0.00 | 0.00 | 0.00 | 0.00 | 0.00 |
| pH | 3.5 | 3.5 | 3.5 | 3.5 | 3.5 | 3.5 |
| Water | Q.S. | Q.S. | Q.S. | Q.S. | Q.S. | Q.S. |
| ratio of SLS/CAPB | 9:1 | 8.5:1.5 | 8:2 | 7.5:2.5 | 7:3 | 6:4 |
| Product Viscosity (cps) | 0 | 0 | 4,662 | 3,447 | 900 | 400 |

Examples Ex. 1 and Ex. 2 showed compared to the comparative examples, that the weight ratio of sodium lauryl sulfate to the co-surfactant comprising cocamidopropyl betaine can directly impact the viscosity and reach the target viscosity of 6,000 cps (6 Pa·s) which is consumer acceptable. If the weight ratio of sodium lauryl sulfate to the co-surfactant is too high, namely above 5:1, the viscosity of the antibacterial cleansing composition falls, which can make it too thin to be consumer acceptable and cannot deliver the antibacterial active chloroxylenol onto skin.

Also, the above results showed that when the weight ratio of sodium lauryl sulfate to the co-surfactant comprising cocamidopropyl betaine is to low, namely below 3:1, the viscosity is from 400-900 cps, which cannot be consumer acceptable and cannot deliver the antibacterial active chloroxylenol onto skin.

The same results were obtained by increasing the fragrance level at 0.02%, 0.40% and at 0.60% when there is an optional desire to add a fragrance to the antibacterial cleansing composition.

The following examples were prepared with fragrance at different levels:

Compositions (wt. %)

|  | C. Ex. E | C. Ex. F | Ex. 3 | Ex. 4 | C. Ex. G | C. Ex. H |
|---|---|---|---|---|---|---|
| Sodium Lauryl Sulfate (SLS)[1] | 9.00 | 8.50 | 8.00 | 7.50 | 7.00 | 6.00 |
| Cocamidopropyl Betaine (CAPB)[2] | 1.00 | 1.50 | 2.00 | 2.50 | 3.00 | 4.00 |
| Sodium benzoate | 0.25 | 0.25 | 0.25 | 0.25 | 0.25 | 0.25 |
| Disodium EDTA | 0.10 | 0.10 | 0.10 | 0.10 | 0.10 | 0.10 |
| Chloroxylenol[3] | 0.50 | 0.50 | 0.50 | 0.50 | 0.50 | 0.50 |
| Citric Acid | 1.30 | 1.30 | 1.30 | 1.30 | 1.30 | 1.30 |
| Benzyl Alcohol | 0.30 | 0.30 | 0.30 | 0.30 | 0.30 | 0.30 |
| Methylchloroisothiazolinone, Methylisothiazolinone[4] | 0.03 | 0.03 | 0.03 | 0.03 | 0.03 | 0.03 |
| Fragrance | 0.20 | 0.20 | 0.20 | 0.20 | 0.20 | 0.20 |
| pH | 3.5 | 3.5 | 3.5 | 3.5 | 3.5 | 3.5 |
| Water | Q.S. | Q.S. | Q.S. | Q.S. | Q.S. | Q.S. |
| ratio of SLS/CAPB | 9:1 | 8.5:1.5 | 8:2 | 7.5:2.5 | 7:3 | 6:4 |
| Product Viscosity (cps) | 0 | 0 | 12,347 | 16,180 | 0 | 1,000 |

|  | C. Ex. I | C. Ex. J | Ex. 5 | Ex. 6 | C. Ex. K | C. Ex. L |
|---|---|---|---|---|---|---|
| Sodium Lauryl Sulfate (SLS)[1] | 9.00 | 8.50 | 8.00 | 7.50 | 7.00 | 6.00 |
| Cocamidopropyl Betaine (CAPB)[2] | 1.00 | 1.50 | 2.00 | 2.50 | 3.00 | 4.00 |
| Sodium benzoate | 0.25 | 0.25 | 0.25 | 0.25 | 0.25 | 0.25 |
| Disodium EDTA | 0.10 | 0.10 | 0.10 | 0.10 | 0.10 | 0.10 |
| Chloroxylenol[3] | 0.50 | 0.50 | 0.50 | 0.50 | 0.50 | 0.50 |
| Citric Acid | 1.30 | 1.30 | 1.30 | 1.30 | 1.30 | 1.30 |
| Benzyl Alcohol | 0.30 | 0.30 | 0.30 | 0.30 | 0.30 | 0.30 |
| Methylchloroisothiazolinone, Methylisothiazolinone[4] | 0.03 | 0.03 | 0.03 | 0.03 | 0.03 | 0.03 |
| Fragrance | 0.40 | 0.40 | 0.40 | 0.40 | 0.40 | 0.40 |
| pH | 3.5 | 3.5 | 3.5 | 3.5 | 3.5 | 3.5 |
| Water | Q.S. | Q.S. | Q.S. | Q.S. | Q.S. | Q.S. |
| ratio of SLS/CAPB | 9:1 | 8.5:1.5 | 8:2 | 7.5:2.5 | 7:3 | 6:4 |
| Product Viscosity (cps) | 0 | 0 | 15,000 | 24,138 | 0 | 1,000 |

|  | C. Ex. K | C. Ex. M | Ex. 7 | Ex. 8 | C. Ex. N | C. Ex. O |
|---|---|---|---|---|---|---|
| Sodium Lauryl Sulfate (SLS)[1] | 9.00 | 8.50 | 8.00 | 7.50 | 7.00 | 6.00 |
| Cocamidopropyl Betaine (CAPB)[2] | 1.00 | 1.50 | 2.00 | 2.50 | 3.00 | 4.00 |
| Sodium benzoate | 0.25 | 0.25 | 0.25 | 0.25 | 0.25 | 0.25 |
| Disodium EDTA | 0.10 | 0.10 | 0.10 | 0.10 | 0.10 | 0.10 |
| Chloroxylenol[3] | 0.50 | 0.50 | 0.50 | 0.50 | 0.50 | 0.50 |
| Citric Acid | 1.30 | 1.30 | 1.30 | 1.30 | 1.30 | 1.30 |
| Benzyl Alcohol | 0.30 | 0.30 | 0.30 | 0.30 | 0.30 | 0.30 |
| Methylchloroisothiazolinone, Methylisothiazolinone[4] | 0.03 | 0.03 | 0.03 | 0.03 | 0.03 | 0.03 |
| Fragrance | 0.60 | 0.60 | 0.60 | 0.60 | 0.60 | 0.60 |
| pH | 3.5 | 3.5 | 3.5 | 3.5 | 3.5 | 3.5 |

-continued

|  | C. Ex. K | C. Ex. M | Ex. 7 | Ex. 8 | C. Ex. N | C. Ex. O |
|---|---|---|---|---|---|---|
| Water | Q.S. | Q.S. | Q.S. | Q.S. | Q.S. | Q.S. |
| ratio of SLS/CAPB | 9:1 | 8.5:1.5 | 8:2 | 7.5:2.5 | 7:3 | 6:4 |
| Product Viscosity (cps) | 0 | 0 | 6,000 | 22,529 | — | — |

The antibacterial cleansing composition Ex. 9 has been assessed in terms of in-vitro time-kill efficacy using the Time-Kill Test Method.

Compositions (wt. %)

|  | Ex. 9 |
|---|---|
| Sodium Lauryl Sulfate (SLS)[1] | 8.00 |
| Cocamidopropyl Betaine (CAPB)[2] | 2.00 |
| Sodium benzoate | 0.25 |
| Disodium EDTA | 0.10 |
| Chloroxylenol[3] | 0.50 |
| Citric Acid | 1.30 |
| Benzyl Alcohol | 0.30 |

-continued

|  | Ex. 9 |
|---|---|
| Methylchloroisothiazolinone, Methylisothiazolinone[4] | 0.03 |
| Pyrrolidone carboxylic acid[5] | 0.03 |
| Salicylic acid | 0.20 |
| Fragrance | 0.40 |
| pH | 3.3 |
| Water | Q.S. |
| ratio of SLS/CAPB | 8:2 |
| Product Viscosity (cps) | 6,000 |

[1]Available from Procter & Gamble
[2]Available from BASF®
[3]Available from Thermo Scientific
[4]Kathon ™ CG, available from Rohm & Hass
[5]AJIDEW ® A100, available from Ajinomoto ® Co., Inc.

TABLE 2 in-vitro Time-Kill efficacy of the antibacterial cleansing composition Ex. 9

| Time Kill Study (Study number: QL370309) | 30seconds (n = 3) | 60seconds (n = 3) |
|---|---|---|
| *Campylobacter jejuni* ATCC 33291 | >5log | >5log |
| *Campylobacter jejuni* ATCC 49943 | >5log | >5log |
| *Enterococcus faecalis* ATCC 19433 | >5log | >5log |
| *Enterococcus faecalis* ATCC 29212 | >5log | >5log |
| *Escherichia coli* ATCC 11775 | >5log | >5log |
| *Escherichia coli* ATCC 25922 | >5log | >5log |
| *Listeria monocytogenes* ATCC 7644 | >5log | >5log |
| *Listeria monocytogenes* ATCC 19115 | >5log | >5log |
| *Pseudomonas aeruginosa* ATCC 15442 | >5log | >5log |
| *Pseudomonas aeruginosa* ATCC 27853 | >5log | >5log |
| *Salmonella enterica serovar Enteritidis* ATCC 13076 | >5log | >5log |
| *Salmonella enterica serovar Typhimurium* ATCC 14028 | >5log | >5log |
| *Shigella sonnei* ATCC 9290 | >5log | >5log |
| *Shigella sonnei* ATCC 25931 | >5log | >5log |
| *Staphylococcus aureus* ATCC 6538 | >5log | >5log |
| *Staphylococcus aureus* ATCC 29213 | >5log | >5log |
| *Methicillin-resistant Staphylococcus aureus* (MRSA) ATCC 33591 | >5log | >5log |
| *Methicillin-resistant Staphylococcus aureus* (MRSA) ATCC 33592 | >5log | >5log |
| *Streptococcus pyogenes* ATCC 14289 | >5log | >5log |
| *Streptococcus pyogenes* ATCC 19615 | >5log | >5log |

TABLE 3

Time-Kill evaluation of Ex. 9 at a contact time of 30 s

| Challenge Organism | Units | Population Control (CFU/mL) | 30 Second Contact Time- Rep. 1 | 30 Second Contact Time- Rep. 2 | 30 Second Contact Time- Rep. 3 |
|---|---|---|---|---|---|
| *Campylobacter jejuni* ATCC 33291 | CFU/mL | $5.3 \times 10^6$ | <10 | <10 | <10 |
|  | Log CFU/mL | 6.7243 | <1.0000 | <1.0000 | <1.0000 |
|  | % reduction |  | >99.999811 | >99.999811 | >99.999811 |
|  | $Log_{10}$ reduction |  | >5.7243 | >5.7243 | >5.7243 |
| *Campylobacter jejuni* ATCC 49943 | CFU/mL | $5.5 \times 10^6$ | <10 | <10 | <10 |
|  | Log CFU/mL | 6.7404 | <1.0000 | <1.0000 | <1.0000 |
|  | % reduction |  | >99.999818 | >99.999818 | >99.999818 |
|  | $Log_{10}$ reduction |  | >5.7404 | >5.7404 | >5.7404 |

TABLE 3-continued

Time-Kill evaluation of Ex. 9 at a contact time of 30 s

| Challenge Organism | Units | Population Control (CFU/mL) | 30 Second Contact Time- Rep. 1 | 30 Second Contact Time- Rep. 2 | 30 Second Contact Time- Rep. 3 |
|---|---|---|---|---|---|
| Enterococcus faecalis ATCC 19433 | CFU/mL Log CFU/mL % reduction $Log_{10}$ reduction | $1.6 \times 10^7$ 7.2041 | <10 <1.0000 >99.999938 >6.2041 | <10 <1.0000 >99.999938 >6.2041 | <10 <1.0000 >99.999938 >6.2041 |
| Enterococcus faecalis ATCC 29212 | CFU/mL Log CFU/mL % reduction $Log_{10}$ reduction | $1.9 \times 10^7$ 7.2788 | <10 <1.0000 >99.999947 >6.2788 | <10 <1.0000 >99.999947 >6.2788 | <10 <1.0000 >99.999947 >6.2788 |
| Escherichia coli ATCC 11775 | CFU/mL Log CFU/mL % reduction $Log_{10}$ reduction | $1.8 \times 10^7$ 7.2553 | <10 <1.0000 >99.999944 >6.2553 | <10 <1.0000 >99.999944 >6.2553 | <10 <1.0000 >99.999944 >6.2553 |
| Escherichia coli ATCC 25922 | CFU/mL Log CFU/mL % reduction $Log_{10}$ reduction | $8.3 \times 10^6$ 6.9191 | <10 <1.0000 >99.999880 >5.9191 | <10 <1.0000 >99.999880 >5.9191 | <10 <1.0000 >99.999880 >5.9191 |
| Listeria monocytogenes ATCC 7644 | CFU/mL Log CFU/mL % reduction $Log_{10}$ reduction | $1.9 \times 10^7$ 7.2788 | <10 <1.0000 >99.999947 >6.2788 | <10 <1.0000 >99.999947 >6.2788 | <10 <1.0000 >99.999947 >6.2788 |
| Listeria monocytogenes ATCC 19115 | CFU/mL Log CFU/mL % reduction $Log_{10}$ reduction | $2.6 \times 10^7$ 7.4150 | <10 <1.0000 >99.999962 >6.4150 | <10 <1.0000 >99.999962 >6.4150 | <10 <1.0000 >99.999962 >6.4150 |
| Pseudomonas aeruginosa ATCC 15442 | CFU/mL Log CFU/mL % reduction $Log_{10}$ reduction | $2.9 \times 10^7$ 7.4624 | <10 <1.0000 >99.999966 >6.4624 | <10 <1.0000 >99.999966 >6.4624 | <10 <1.0000 >99.999966 >6.4624 |
| Pseudomonas aeruginosa ATCC 27853 | CFU/mL Log CFU/mL % reduction $Log_{10}$ reduction | $1.4 \times 10^7$ 7.1461 | <10 <1.0000 >99.999929 >6.1461 | <10 <1.0000 >99.999929 >6.1461 | <10 <1.0000 >99.999929 >6.1461 |
| Salmonella enterica serovar Enteridis ATCC 13076 | CFU/mL Log CFU/mL % reduction $Log_{10}$ reduction | $2.3 \times 10^7$ 7.3617 | <10 <1.0000 >99.999957 >6.3617 | <10 <1.0000 >99.999957 >6.3617 | <10 <1.0000 >99.999957 >6.3617 |
| Salmonella enterica serovar Typhimurium ATCC 14028 | CFU/mL Log CFU/mL % reduction $Log_{10}$ reduction | $7.3 \times 10^6$ 6.8633 | <10 <1.0000 >99.999863 >5.8633 | <10 <1.0000 >99.999863 >5.8633 | <10 <1.0000 >99.999863 >5.8633 |
| Shigella sonnei ATCC 9290 | CFU/mL Log CFU/mL % reduction $Log_{10}$ reduction | $2.5 \times 10^7$ 7.3979 | <10 <1.0000 >99.999960 >6.3979 | <10 <1.0000 >99.999960 >6.3979 | <10 <1.0000 >99.999960 >6.3979 |
| Shigella sonnei ATCC 25931 | CFU/mL Log CFU/mL % reduction $Log_{10}$ reduction | $2.1 \times 10^8$ 8.3222 | <10 <1.0000 >99.999995 >7.3222 | <10 <1.0000 >99.999995 >7.3222 | <10 <1.0000 >99.999995 >7.3222 |
| Staphylococcus aureus ATCC 6538 | CFU/mL Log CFU/mL % reduction $Log_{10}$ reduction | $7.8 \times 10^7$ 7.8921 | <10 <1.0000 >99.999987 >6.8921 | <10 <1.0000 >99.999987 >6.8921 | <10 <1.0000 >99.999987 >6.8921 |
| Staphylococcus aureus ATCC 29213 | CFU/mL Log CFU/mL % reduction $Log_{10}$ reduction | $8.7 \times 10^7$ 7.9395 | <10 <1.0000 >99.999989 >6.9395 | <10 <1.0000 >99.999989 >6.9395 | <10 <1.0000 >99.999989 >6.9395 |

TABLE 3-continued

Time-Kill evaluation of Ex. 9 at a contact time of 30 s

| Challenge Organism | Units | Population Control (CFU/mL) | 30 Second Contact Time- Rep. 1 | 30 Second Contact Time- Rep. 2 | 30 Second Contact Time- Rep. 3 |
|---|---|---|---|---|---|
| Methicillin-resistant Staphylococcus aureus (MRSA) ATCC 33591 | CFU/mL Log CFU/mL % reduction $Log_{10}$ reduction | $3.1 \times 10^7$ 7.4914 | <10 <1.0000 >99.999968 >6.4914 | <10 <1.0000 >99.999968 >6.4914 | <10 <1.0000 >99.999968 >6.4914 |
| Methicillin-resistant Staphylococcus aureus (MRSA) ATCC 33592 | CFU/mL Log CFU/mL % reduction $Log_{10}$ reduction | $6.7 \times 10^7$ 7.8261 | <10 <1.0000 >99.999985 >6.8261 | <10 <1.0000 >99.999985 >6.8261 | <10 <1.0000 >99.999985 >6.8261 |
| Streptococcus pyogenes ATCC 14289 | CFU/mL Log CFU/mL % reduction $Log_{10}$ reduction | $5.6 \times 10^7$ 7.7482 | <10 <1.0000 >99.999982 >6.7482 | <10 <1.0000 >99.999982 >6.7482 | <10 <1.0000 >99.999982 >6.7482 |
| Streptococcus pyogenes ATCC 19615 | CFU/mL Log CFU/mL % reduction $Log_{10}$ reduction | $8.5 \times 10^6$ 6.9294 | <10 <1.0000 >99.999882 >5.9294 | <10 <1.0000 >99.999882 >5.9294 | <10 <1.0000 >99.999882 >5.9294 |

Similar results were obtained for Time-Kill evaluation of Ex. 9 at a contact time of 60 s

TABLE 4

Ex. 9 Neutralizer Effectiveness and Toxicity Test Results (CFU/mL)

| Challenge Organism | Neutralizer Effectiveness Test[1]* $Log_{10}$ Difference | Neutralizer Toxicity Test[1]* $Log_{10}$ Difference |
|---|---|---|
| Staphylococcus aureus ATCC 6538 | 0.0010 | −0.0727 |
| Escherichia coli ATCC 11775 | −0.0253 | 0.0611 |
| Campylobacter jejuni ATCC 33291 | 0.0076 | −0.0448 |

[1]No statistically significant difference observed during testing between initial and final time points (<0.2 $Log_{10}$).

TABLE 5

Ex. 9 Neutralizer Effectiveness and Toxicity Tests

| Challenge Organism | Neutralizer Effectiveness Test vs. Test Organism Viability p-value[1]* | Neutralizer Toxicity Test vs. Test Organism Viability p-value[1]* |
|---|---|---|
| Staphylococcus aureus ATCC 6538 | 0.0010 | −0.0727 |
| Escherichia coli ATCC 11775 | −0.0253 | 0.0611 |
| Campylobacter jejuni ATCC 33291 | 0.0076 | −0.0448 |

[1]A t-test comparing NET and NTT to the TOV indicated no statistical significance (p > 0.05).

The above results showed consistent antibacterial efficacy, delivering >5 log reduction for all challenged microorganisms at both 30 seconds and 60 seconds contact time with the composition of Ex. 9 comprising 0.5 wt. % of chloroxylenol, which meets the minimum >3 log reduction as required in the FDA monograph.

In other words, based on the results, for Ex. 9, at least a 5-log or 99.999% reduction was observed for the 30 second and 60 second contact time intervals for all challenge microorganisms tested. The start and end counts for test culture viability were within ±0.5 $Log_{10}$.

The recovery of organisms from the Neutralizer Effectiveness and Neutralizer Toxicity Tests was not significantly different from the recovery of organisms from the Test Organism Viability (p>0.05). All media controls passed specification.

Additional Examples/Combinations

A. An antibacterial cleansing composition comprising:
    a) from 0.01% to 1% of chloroxylenol by weight of the composition;
    b) from 5% to 15% of sodium lauryl sulfate by weight of the composition;
    c) from 1% to 5% of a co-surfactant by weight of the composition, wherein the co-surfactant is selected from zwitterionic surfactant, amphoteric surfactant, nonionic surfactant, or combinations thereof;
    d) wherein the weight ratio of sodium lauryl sulfate to the co-surfactant ranges from 3:1 to 5:1; preferably from 7.5:2.5 to 8:2; and
    e) wherein the composition comprises a pH of from 2 to 5.

B. The antibacterial cleansing composition of Paragraph A, comprising from 0.10% to 0.75% of chloroxylenol by weight of the composition; preferably from 0.40% to 0.60% of chloroxylenol by weight of the composition.

C. The antibacterial cleansing composition of any of the preceding Paragraphs, comprising from about 0.005% to about 5% of pyrrolidone carboxylic acid by weight of the composition; preferably from 0.02% to 1% of pyrrolidone carboxylic acid by weight of the composition; more preferably from 0.025% to 0.15% of pyrrolidone carboxylic acid by weight of the composition; even more preferably from about 0.025% to about 0.05% of pyrrolidone carboxylic acid by weight of the composition; most preferably from about 0.025% to about 0.035% of pyrrolidone carboxylic acid by weight of the composition.

D. The antibacterial cleansing composition of any of the preceding Paragraphs, wherein the composition comprises from 7% to 9% of sodium lauryl sulfate by weight of the composition; preferably wherein the composition comprises from 7.5% to 8% of sodium lauryl sulfate by weight of the composition.

E. The antibacterial cleansing composition of any of the preceding Paragraphs, wherein the composition comprises from 8% to 10% of sodium lauryl sulfate and wherein the antibacterial cleansing composition is a liquid hand wash composition.

F. The antibacterial cleansing composition of any of the preceding Paragraphs, wherein the composition comprises from 1.4% to 3.0% of a co-surfactant by weight of the composition; preferably from 2.0% to 2.5% of a co-surfactant by weight of the composition.

G. The antibacterial cleansing composition of any of the preceding Paragraphs, wherein the composition comprises from 7.5% to 8% of sodium lauryl sulfate by weight of the composition and from 2.0% to 2.5% of a co-surfactant by weight of the composition.

H. The antibacterial cleansing composition of any of the preceding Paragraphs, wherein the co-surfactant comprises cocamidopropyl betaine.

I. The antibacterial cleansing composition of Paragraph H, wherein the antibacterial cleansing composition has a weight ratio of sodium lauryl sulfate to cocamidopropyl betaine ranging from 3:1 to 5:1; preferably from 7.5:2.5 to 8:2; more preferably of 8:2.

J. The antibacterial cleansing composition of any of the preceding Paragraphs, wherein the pH is from 3 to 3.5.

K. The antibacterial cleansing composition of any of the preceding Paragraphs, having a viscosity from 2.75 Pa·s (2,750 cps) to 30 Pa·s (30,000 cps); preferably from 3 Pa·s (3,000 cps) to 25 Pa·s (25,000 cps); more preferably from 3.4 Pa·s (3,400 cps) to 24.25 Pa·s (24,250 cps) as measured according to the Cone/Plate Viscosity Measurement Test Method as disclosed herein.

L. A method of washing hands and washing away 99% of bacteria comprising the following steps in that order:
   a) providing a container adapted to contain the antibacterial cleansing composition of any of the preceding Paragraphs;
   b) dispensing the antibacterial cleansing composition into palms of a user's hands;
   c) optionally lather by rubbing palms together;
   d) spread the antibacterial cleansing composition across the palms, back of hands, between fingers, and/or under nails;
   e) rinse hands;
   f) optionally dry;
   g) wherein the antibacterial cleansing composition washes away 99% of bacteria.

M. The method of Paragraph L, wherein the container is a pump dispenser or a pump foam dispenser.

N. A liquid hand wash composition comprising:
   a) from 7% to 9%, preferably from 7.5% to 8% of sodium lauryl sulfate by weight of the composition;
   b) from 1.75% to 3%, preferably from 2% to 2.5% of cocamidopropyl betaine by weight of the composition;
   c) wherein the weight ratio of sodium lauryl sulfate and cocamidopropyl betaine ranges from 7.5:2.5 to 8:2;
   d) from 0.40% to 0.60% of chloroxylenol by weight of the composition; and
   wherein the composition comprises a pH of from 4 to 5 and a viscosity of from 5 Pa·s (5000 cps) to 10 Pa·s (10,000 cps) as measured according to the Cone/Plate Viscosity Measurement Test Method as disclosed herein.

O. The liquid hand wash composition of any of the preceding Paragraph N, comprising from 0.025% to 0.035% of pyrrolidone carboxylic acid by weight of the composition.

P. The liquid hand wash composition of any of the preceding Paragraphs N to O, wherein the liquid hand wash composition comprises 8% sodium lauryl sulfate, 2% cocamidopropyl betaine, and 0.05% of chloroxylenol; preferably wherein the liquid hand wash composition comprises 8% sodium lauryl sulfate, 2% cocamidopropyl betaine, 0.03% pyrrolidone carboxylic acid and 0.05% of chloroxylenol.

Q. An antibacterial cleansing composition of any of the preceding Paragraphs A-K for use as an antibacterial medicament in the form of a product to be applied to the human skin.

R. The antibacterial cleansing composition of any of the preceding Paragraphs A-K for use in a method of inhibiting or killing the growth of bacteria onto human skin; preferably for use in a method of inhibiting or killing the growth of bacteria onto human skin, wherein the bacteria is *Staphylococcus aureus*.

S. The antibacterial cleansing composition of any of the preceding Paragraphs A-K for use in a method of inhibiting or killing the growth of bacteria onto human skin, wherein the bacteria is one as listed in Table 1 as detailed herein.

T. Non-therapeutic use of the antibacterial cleansing composition of any of the preceding Paragraphs A-K for providing a cleansing benefit.

U. Non-therapeutic use of the antibacterial cleansing composition of any of the preceding Paragraphs A-K for improving hand hygiene.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antibacterial cleansing composition comprising:
   a) from about 0.01% to about 1% of chloroxylenol by weight of the composition;
   b) from about 5% to about 15% of sodium lauryl sulfate by weight of the composition;
   c) from about 1% to about 5% of a co-surfactant by weight of the composition, wherein the co-surfactant is chosen from zwitterionic surfactant, amphoteric surfactant, nonionic surfactant, or mixtures thereof;
   d) wherein the weight ratio of sodium lauryl sulfate to the co-surfactant ranges from about 3:1 to about 5:1; and wherein the composition comprises a pH of from about 2 to about 5.

2. The antibacterial cleansing composition of claim 1, comprising from about 0.10% to about 0.75% of chloroxylenol by weight of the composition.

3. The antibacterial cleansing composition of claim 2, comprising from about 0.40% to about 0.60% of chloroxylenol by weight of the composition.

4. The antibacterial cleansing composition of claim 1, comprising from about 0.005% to about 5% of pyrrolidone carboxylic acid by weight of the composition.

5. The antibacterial cleansing composition of claim 1, wherein the composition comprises from about 7% to about 9% of sodium lauryl sulfate and wherein the antibacterial cleansing composition is a liquid hand wash composition.

6. The antibacterial cleansing composition of claim 1, wherein the composition comprises from about 1.4% to about 3.0% of a co-surfactant by weight of the composition.

7. The antibacterial cleansing composition of claim 6, wherein the co-surfactant comprises cocamidopropyl betaine.

8. The antibacterial cleansing composition of claim 7, wherein the antibacterial cleansing composition has a weight ratio of sodium lauryl sulfate to cocamidopropyl betaine ranging from about 3:1 to about 5:1.

9. The antibacterial cleansing composition of claim 1, wherein the pH is from about 3 to about 3.5.

10. The antibacterial cleansing composition of claim 1, having a viscosity from about 2,750 cps to about 30,000 cps.

11. The antibacterial cleansing composition of claim 1, wherein the viscosity is from about 5000 cps to about 10,000 cps.

12. A method of washing hands and washing away about 99% of bacteria comprising the following steps in that order:
   a) providing a container adapted to contain the antibacterial cleansing composition of claim 1;
   b) dispensing the antibacterial cleansing composition into palms of a user's hands;
   c) lather by rubbing palms together;
   d) spread the antibacterial cleansing composition across the palms, back of hands, between fingers, and/or under nails;
   e) rinse hands;
   f) dry;
   g) wherein the antibacterial cleansing composition washes away about 99% of bacteria.

13. The method of claim 12, wherein the container is a pump dispenser or a pump foam dispenser.

14. A liquid hand wash composition comprising:
   a) from about 7% to about 9% of sodium lauryl sulfate by weight of the composition;
   b) from about 1.75% to about 3% of cocamidopropyl betaine by weight of the composition;
   c) wherein the weight ratio of sodium lauryl sulfate to cocamidopropyl betaine ranges from about 7.5:2.5 to about 8:2;
   d) from about 0.40% to about 0.60% of chloroxylenol by weight of the composition; and
      wherein the composition comprises a pH of from about 4 to about 5 and a viscosity of from about 3,000 cps to about 25,000 cps.

15. The liquid hand wash composition of claim 14, wherein the liquid hand wash composition comprises about 8% sodium lauryl sulfate, about 2% cocamidopropyl betaine, and about 0.05% of chloroxylenol.

* * * * *